United States Patent [19]

Michaely et al.

[11] Patent Number: 5,430,007
[45] Date of Patent: Jul. 4, 1995

[54] CERTAIN HERBICIDAL PYRAZOLOPYRIDAZINES

[75] Inventors: William J. Michaely, El Cerrito; Jeff K. Curtis, San Anselmo; Christopher G. Knudsen, Berkeley, all of Calif.

[73] Assignee: Zeneca Limited, Millbank, England

[21] Appl. No.: 176,059

[22] Filed: Jan. 3, 1994

Related U.S. Application Data

[62] Division of Ser. No. 010,204, Jan. 28, 1993, Pat. No. 5,300,478.

[51] Int. Cl.[6] .................... A91N 43/90; C07D 487/04
[52] U.S. Cl. .................... 504/236; 504/237; 504/238; 544/236
[58] Field of Search ............... 544/236, 262; 504/236, 504/237, 238

[56] References Cited

U.S. PATENT DOCUMENTS

| | | | |
|---|---|---|---|
| 4,124,374 | 11/1978 | Wolf et al. | 544/175 |
| 5,167,691 | 12/1992 | Maravetz | 504/282 |
| 5,169,850 | 12/1992 | Dusza et al. | 514/258 |

FOREIGN PATENT DOCUMENTS

| | | |
|---|---|---|
| 509717 | 10/1992 | European Pat. Off. . |
| 2235941 | 1/1975 | France . |
| 18008 | 9/1993 | WIPO . |

OTHER PUBLICATIONS

Chemical Abstracts, 77: 48325b, "1H–Pyrazolo[3,4–b]-pyridines", Hoehn, H., J. Heterocycl. Chem. 1972, 9(2) pp. 235–253.

*Primary Examiner*—Bernard Dentz
*Attorney, Agent, or Firm*—Marian T. Thomson

[57] ABSTRACT

Novel substituted pyrazolo-rings fused to nitrogen containing heterocyclic rings having the following formula

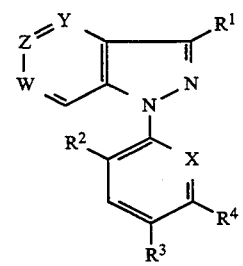

in which at least one of Y, Z or W is N or N-O and the remainder of Y, Z or W is C-R wherein the remainder of the variables are as defined in the specification and agriculturally effective salts thereof are herbicides.

11 Claims, No Drawings

CERTAIN HERBICIDAL PYRAZOLOPYRIDAZINES

This is a divisional, of application Ser. No. 08/010,204, filed Jan. 28, 1993 now U.S. Pat. No. 5,300,478.

BACKGROUND AND SUMMARY OF THE INVENTION

This invention relates to novel substituted pyrazolo-rings fused to nitrogen containing heterocyclic rings having the following formula:

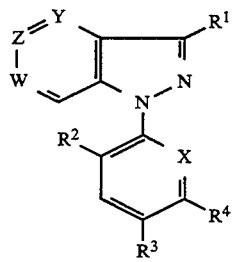

in which at least one of Y, Z or W is N or N-O and the remainder of Y, Z or W is C-R wherein R is hydrogen; halogen; nitro; cyano; alkyl; alkoxymethyl; acetoxymethyl; hydroxymethyl; haloalkyl; formyl; alkylcarbonyl; carboxy and its salts; COO alkyl; azido ($N_3$); amino; substituted amino wherein the substituents are alkyl, alkoxy, hydroxy, formyl, alkylcarbonyl, alkoxycarbonylalkyl-oxy, alkoxycarbonylalkylthio, alkoxycarbonylalkylidenecarbonyl, hydroxycarbonylalkoxy, hydroxycarbonylthio, cyanoalkoxy, hydroxycarbonylalkyledinecarbonyl, alkylsulfonyl, haloalkylsulfonyl, aminocarbonyl, (di)alkylaminocarbonyl, alkoxycarbonyl, alkoxyalkyl, hydroxycarbonylalkyl, alkoxycarbonylalkyl, and amino; carboxyamido; substituted carboxyamido wherein said substituents can be selected from alkyl, alkylsulfonyl, and haloalkylsulfonyl; sulfonamido wherein the N is substituted with hydrogen and/or alkyl; $VR^6$ wherein V is O and $S(O)_m$ and $R^6$ is selected from the group hydrogen, alkyl, haloalkyl, cyanoalkyl, alkoxycarbonylalkyl, hydroxycarbonylalkyl and aminocarbonylalkyl wherein the N is substituted with hydrogen and/or alkyl;

m is 0 to 2;

$R^1$ is hydrogen and halogen;

$R^2$ is hydrogen, nitro, halogen, cyano, alkylthio, alkylsulfinyl, alkylsulfonyl, and alkoxy;

$R^3$ is halogen, haloalkyl, cyano, alkylthio, alkylsulfinyl, and alkylsulfonyl;

$R^4$ is hydrogen and halogen;

X is N or C-$R^5$;

wherein $R^5$ is hydrogen, haloalkyl, halogen, cyano, nitro, alkythio, alkylsulfinyl, alkylsulfonyl, and alkoxy; and agriculturally acceptable salts thereof.

DESCRIPTION OF THE INVENTION

Within the scope of the above invention, certain embodiments are preferred as follows:

R is preferably halogen, nitro, cyano, lower alkyl, lower haloalkyl, alkoxy, alkoxyalkyl, alkylsulfonyl, alkoxycarbonylalkylthio, and alkythio. More particularly preferred groups are chloro, bromo, methyl, ethyl, trifluoromethyl, cyano, ethylthio, ethyl sulfonyl and alkoxycarbonylalkylthio.

$R^1$ is hydrogen.

$R^2$ is halogen. Particularly preferred is chloro or fluoro.

$R^3$ is halo or haloalkyl. Particularly preferred is trifluoromethyl.

$R^4$ is hydrogen.

X is preferably N or C-halogen particularly C-chloro.

The term "alkyl" and all groups containing alkyl portions are intended to include straight-chain, branched-chain and cyclic groups. Examples are methyl, ethyl, n-propyl, isopropyl, cyclopropyl, n-butyl and t-butyl. Each alkyl member may contain one to six carbon atoms. For example ($C_1$-$C_6$)alkoxy($C_1$-$C_6$)alkoxy.

In the above definitions the term "halogen" includes fluoro, chloro, bromo and iodo groups. In polyhalogenated groups the halogens may be the same or different. The term haloalkyl refers to the alkyl group substituted by one or more halogen atoms.

The compounds of the present invention, have been found to be active herbicides, possessing utility as preemergence and post-emergence herbicides and useful against a wide range of plant species including broadleaf and grassy species.

This invention therefore also relates to a method for controlling undesirable vegetation comprising applying to a locus where control of such vegetation is desired, either prior or subsequent to the emergence of such vegetation, a herbicidally effective amount of a compound as described herein, together with an inert diluent or carrier suitable for use with herbicides.

The terms "herbicide" and "herbicidal" are used herein to denote the inhibitive control or modification of undesired plant growth. Inhibitive control and modification include all deviations from natural development such as, for example, total killing, growth retardation, defoliation, desiccation, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots and above-ground portions. The term "agriculturally acceptable" salt includes sodium, potassium, calcium, ammonium and magnesium salts.

The process for making the compounds of this invention will be more fully understood by reference to the following examples:

EXAMPLE 1

PYRAZOLO [4,3-b]PYRIDINES

Preparation of 5,6-dimethyl-1-[2,6-dichloro-4-trifluoromethylphenyl]-1-H-pyrazolo [4,3-b] pyridine (Compound 1 in Table I)

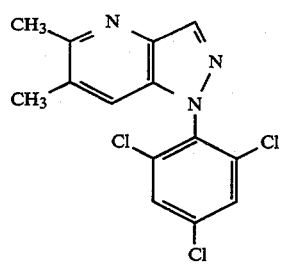

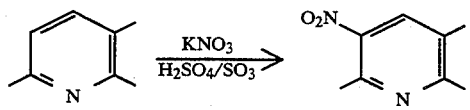

To 200 milliliters (mL) of 20% fuming sulfuric acid, cooled to 0° C., was slowly added 21.20 grams (g) of 2,3,6-tri-methylpyridine. An excess (25%) of solid potassium nitrate was added and the mixture was heated at 100° C. for 8 hours and at 125°-130° C. for 8 hours. The cooled reaction mixture was poured into 2 liters of ice. Solid sodium carbonate was slowly added to the mixture until an organic solid appeared. An additional 20 g of sodium carbonate was added and the solution was extracted twice with ether. The ether extracts were dried and concentrated to give 22.94 g of solid 5-nitro-2,3,6-trimethylpyridine, m.p.=53° C.

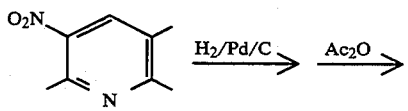

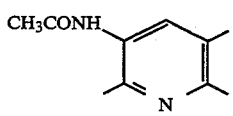

An 18.7 g sample of 5-nitro-2,3,6-trimethylpyridine was dissolved in 200 mL of methanol and 100 mg of 5% palladium on carbon was added. Hydrogenation was performed at 45 lb. and yielded the crude amino compound after 45 minutes. The compound was filtered through diatomaceous earth, concentrated under vacuum, dissolved in 50 mL of methylene chloride, and then 20 mL of acetic anhydride was added. The mixture was heated for 1 hour on a steam bath and poured onto 300 mL of freshly prepared 5% aqueous sodium carbonate. The aqueous solution was extracted with methylene chloride, dried, concentrated under vacuum, and the resulting solid tritiated with pentane to give 18.3 g of 5-(acetylamino) - 2,3,6-tri-methylpyridine, m.p. 89°-92° C.

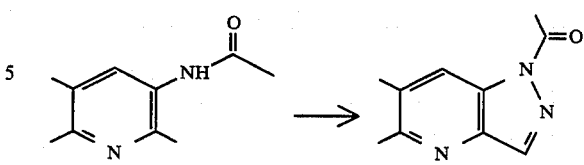

The reaction was run similar to that described by D. Chapman and J. Durst, J. Chem. Soc. Perkin I, 2398 (1980). A 12.40 g sample of the 5-(acetylamino)-2,3,6-trimethylpyridine was combined with 22 mL of acetic anhydride, 22 mL of acetic acid, and 13 g of potassium acetate in 200 mL of benzene. The mixture was brought to reflux. A solution of an excess of amyl nitrite, (11 g) in benzene (40 mL), was added to the refluxing solution over a period of 2 hours and refluxing was continued an additional 12 hours. The reaction was cooled and stirred, with 200 mL of 5% aqueous sodium carbonate, for 3 hours. The organic phase was separated, dried with anhydrous sodium sulfate, concentrated under vacuum and chromatographed (silica gel: methylene chloride/ether) to give 4.94 g of 1-acetyl-5,6-dimethyl-pyrazolo [4,3-b] pyridine.

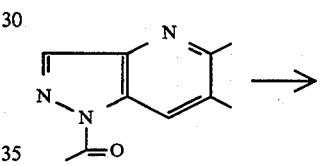

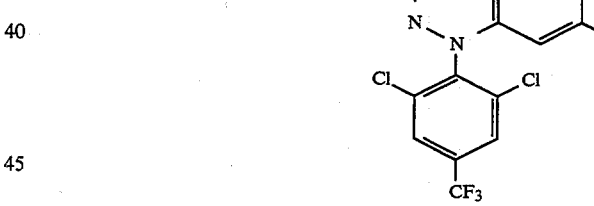

A 3.80 g sample of 1-acetyl-5,6-dimethylpyrazolo [4,3-b] pyridine was heated with 25 mL of 20% aqueous hydrochloric acid for 1½ hours on a steam bath. The aqueous solution was cooled, neutralized and extracted with methylene chloride. The methylene chloride extracts were dried and concentrated to 3.1 g of crude, deacylated pyrazolopyridine. This crude product was dissolved in 40 mL of dimethylformamide and 6 g of powdered potassium carbonate was added along with the addition of 5.4 g 3,5-dichloro-4-fluorobenzotrifluoride. After stirring for 2-72 hours, the reaction was poured into 250 mL of ice water and 150 mL of ether was added. The organic phase was separated, washed twice with water and dried. Chromatography gave 0.891 g of a pure solid, insoluble in pentane. The product, 5,6-dimethyl-l-[2,6-dichlor-4-tri-fluoromethylphenyl]-1-H-pyrazolo [4,3-b] pyridine (Compound No. 1 in Table 1) had m.p.=135°-136° C.

EXAMPLE 2

PYRAZOLO [4,3-c] PYRIDINES PREPARATION OF VARIOUS 1-ARYL-4-METHYL-PYRAZOLO [4,3-c] PYRIDINES

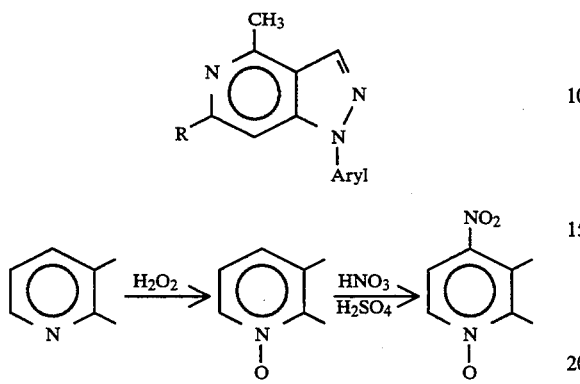

2,3-dimethylpyridine N-oxide

A sample of 175 mL of 30% hydrogen peroxide was added slowly to 100 g 2,3-dimethylpyridine in 1.0 L AcOH. The temperature was kept below 85° C. After the addition was complete, the mixture was gradually heated to 90° C. and after 3 hours stirred at 60° C. for 18 hours. The volume was reduced under vacuum. Yield 130 g N-oxide as a light oil (contaminated by acetic acid). This crude product was used in the next step without further purification.

4-nitro-2,3-dimethylpyridine N-oxide

To 400 mL of concentrated $H_2SO_4$ was added slowly 130 g of impure 2,3-dimethylpyridine N-oxide. Fuming $HNO_3$ (330 mL) was slowly added at a rate to keep the temperature between 120° C. and 170° C. After addition was complete, the temperature was held at 103° C. for 3 hours and then the reaction was cooled. The crude reaction was added to 1 kg ice in a large pan, then, with stirring, 1.1 kg $Na_2CO_3$ was added. After cooling to room temperature, the solids were removed by suction filtration from the solution. The filtrate was extracted with chloroform. The solids were washed with hot chloroform (3 times). The combined reduced organic extracts yielded 110 g of the crude desired nitropyridine N-oxide as an orange solid.

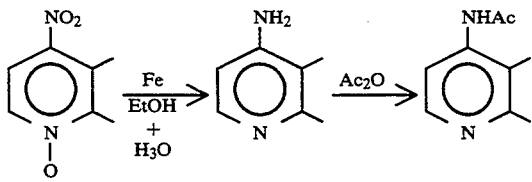

4-acetylamino-2,3-dimethylpyridine

A flask was charged with 50 g of the nitropyridine N-oxide, 200 mL ethanol, 50 mL $H_2O$ and 10 mL concentrate HCl. The solution was heated to near reflux. Iron powder (100 g) was added in portions to the refluxing mixture. The crude product was filtered and washed with hot methanol. The solution was reduced under vacuum to yield 40 g of crude amino pyridine as a dark oil. The above was stirred in excess acetic anhydride overnight at room temperature, then reduced under vacuum. The product was dissolved in 500 mL chloroform and 200 g of solid $K_2CO_3$ added and stirred for 3 hours, filtered and reduced. Product was filtered through silica. Yield, 40 g of the title compound as a tan solid.

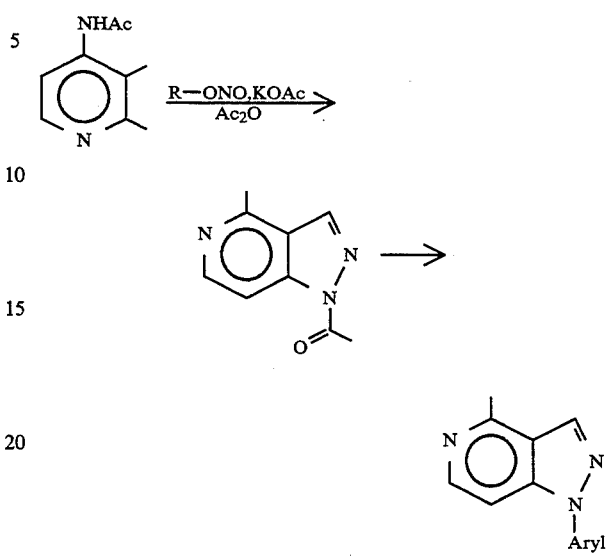

4-methylpyrazolo[4,3-c]pyridines

A sample of the acetylaminopyridine can be converted to the 4-(substituted) methyl pyrazolo [4,3-c]pyridines by the conditions described in Example 1. (Compounds 13, 15, 16, 18 and 27)

The aryl group may be a substituted phenyl or substituted pyridyl ring wherein the substituents are as heretofore defined as $R^2$, $R^3$, $R^4$ and $R^5$.

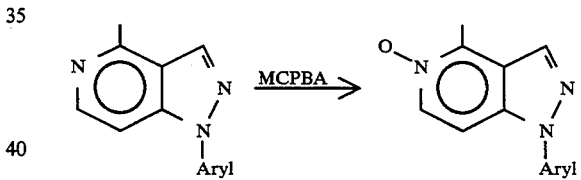

5-oxo-4-methylpyrazolo [4,3-c]pyridine

To a solution of 0.5 g 1-[3-chloro-5-trifluoromethyl -2-pyridyl]-4-methylpyrazolo-[4,3-c]pyridine (Compound No. 13) in methylene chloride at 0° C. was added 0.6 g 50% metachloro-peroxybenzoic acid. The solution was stirred for 18 hours at room temperature, then was washed with 1 mL sodium hydroxide, dried with ($MgSO_4$) and reduced under vacuum to yield 0.6 g 1-[3-chloro-5-trifluoro-methyl-2-pyridyl]-4-methyl-pyrazolo [4,3-c]pyridine-5-(N)-oxide as a tan solid; m.p. 186°–187° C. (Compound No. 16).

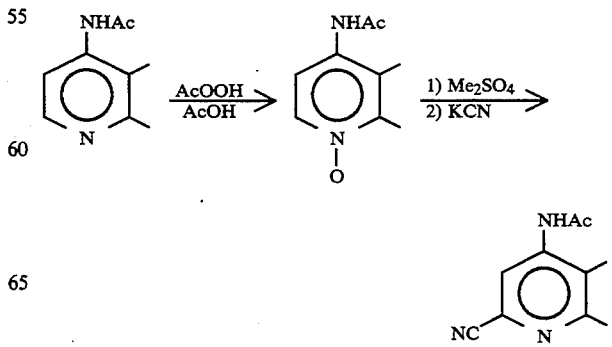

4-acetylamino-2,3-dimethylpyridine N-oxide 200 mL 30% peracetic acid in acetic acid was slowly added to a solution of 50 g 4-acetylamino-2,3-dimethylpyridine in 100 mL glacial acetic acid at 60° C. The solution was held at 70° C. for 12 hours then reduced under vacuum heated by a 50° C. water bath. Yield, 58 g N-oxide.

2-cyano-4-acetylamino-4,5-dimethylpyridine

A solution of 10 g 4-acetylamino-2,3-dimethyl-pyridine N-oxide in 25 g dimethylsulfate was cautiously heated to and maintained at 80° C. for 90 minutes. Reduced under vacuum, dissolved in acetonitrile and added to an ice cold solution of excess potassium cyanide in water. The solution was saturated with sodium chloride and, after stirring 18 hours at room temperature, extracted with chloroform (2 times). The organic extracts were dried (MgSO4) and reduced to 3 g of a mixture. Purified by column chromatography (CH2Cl2/pentane) to yield 1.3 g of the titled cyanopyridine.

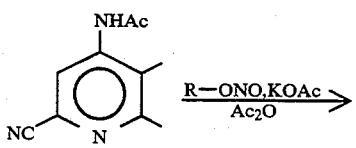

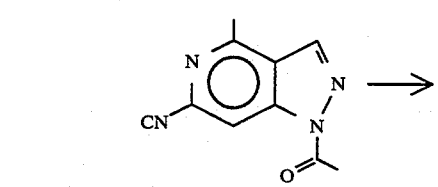

6-cyano-4-methylpyrazolo [4.3-c]pyridines

Using methods previously described in Example 1, 0.6 g 4-acetylamino-2-cyano-5,6-dimethylpyride was converted to the pyrazolopyridine then to the N-arylated pyrazolopyridine. Yield 0.12 g 1-[3-chloro-5-trifluoro-methyl-2-pyridyl]-6-cyano-4-methylpyrazolo [4,3-c]pyridine (Compound No. 14) as a solid; m.p. 144°–145° C. and 0.08 g by product 2-[3-chloro-5-trifluoro-methyl-2-pyridyl]-6-cyano-4-methylpyrazolo [4,3-c]-pyridine as a solid; m.p. 180°–185° C.

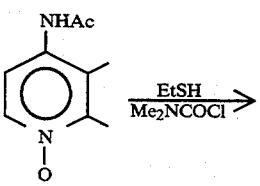

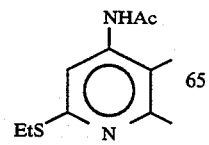

4-acetylamino-2-ethanethio-5,6-dimethylpyridine

To 15 g 4-acetylamino-2,3-dimethylpyridine N-oxide in methylene chloride was added 5 g dimethylcarbamyl chloride and the reacton was stirred for 30 minutes. Dropwise 4.6 g ethanethiol was added and stirred for 3 days at room temperature. The organic layer was washed with 10% NaHCO3, dried (MgSO4) and reduced under vacuum. Purification by column chromatography gave 2.6 g of the ethanethio substituted pyridine.

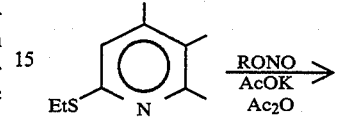

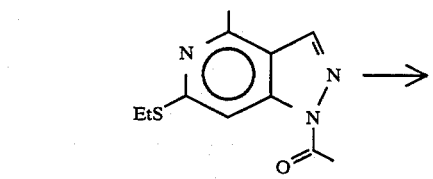

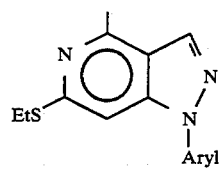

6-ethanethio-4-methylpyrazolo [4,3-c]pyridines

Using methods previously described in Example 1, 1.7 g 4-acetylamino-2-ethanethio-4,5-dimethylpyridine was converted to 0.15 g 1-H-pyrazolapyridine. This was arylated and purified to yield 0.06 g 1-[3-chloro-5-trifluoromethyl-2-pyridyl]-6-ethanethio-4-methyl-pyrazolo-[4,3-c]pyridine (Compound No. 17).

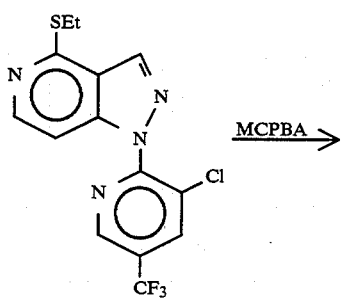

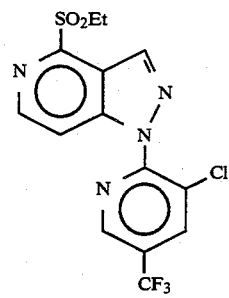

4-ethanesulfonylpyrazolo [4,3-c]pyridine

Meta-chloroperoxybenzoic acid (2.1 eq) was added to the corresponding 6-ethanethio compound (Compound 8) in ice cold methylene chloride and stirred overnight at room temperature. The solution was washed with 1N sodium hydroxide and water; dried and reduced under vacuum to give 1-[3-chloro-5-trifluoromethyl-2-pyridyl]-4-ethanesulfonyl pyrazolo [4,3-c]pyridine (Compound No. 9).

4-hydroxymethyl-1 [3-chloro, 5-trifluoromethyl-2-pyridyl]pyrazolo 4,3-c]pyridine (Compound 27 in Table II)

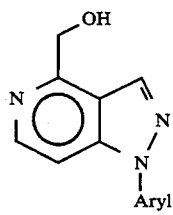

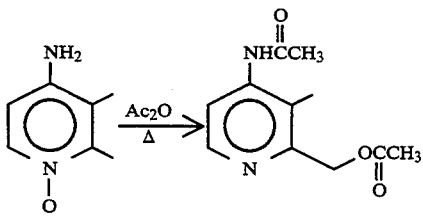

2-acetoxymethyl-4-acetylamino-3-methyl-pyridine

A solution of 8 g (58 mmole) 4-amino-2,3-dimethylpyridine N-oxide in 100 mL acetic anhydride was heated to reflux for 20 minutes; reduced under vacuum to an oil and purified by column chromatography. Yield was 5 g of the title compound as an oil

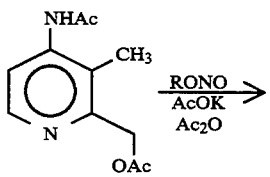

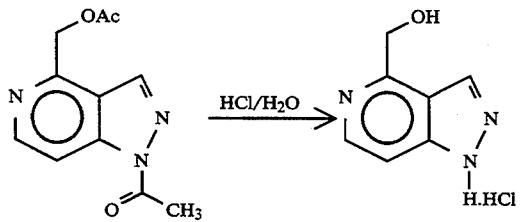

1-H-4-hydroxymethyl-pyrazolo [4.3-c]pyridine hydrochloride

A flask was charged with 5 g of the above described compound, 2.2 g (1 eq) potassium acetate, 4.6 g (2 eq) acetic anhydride and 0.2 g 18-crown-6 in anhydrous benzene. Heated to reflux and added, over 15 minutes, 4.5 g (2 eq) isoamyl nitrite. The solution was allowed to reflux for 5 hours, cooled, washed with saturated NaCl, dried (MgSO4) and purified by column chromatography. Yield was 1.5 g 1-acetyl-4-acetoxymethyl pyrazolo [4,3-c]pyride as a solid.

The above pyrazolopyridine in 20 mL 2M HCl was refluxed, then reduced under vacuum. Yield was 2 g of the title compound as a soft solid.

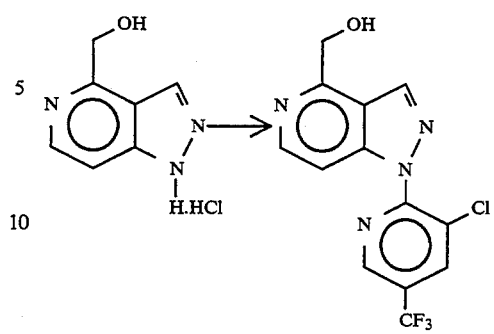

1-[3-chloro-5-trifluoromethyl-2-pyridyl]-4-hydroxymethyl pyrazolo [4,3-c]pyridine Two grams of the above described pyrazolopyridine hydrochloride, 5.0 g potassium carbonate and 5.0 g 2,3-dichloro-5-trifluoromethylpyridine in 20 mL dimethyl formamide was heated to 85° C. for 2 hours. The solution was cooled and diethyl ether was added. Then the solution was washed with saturated NaCl, dried, reduced under vacuum, and purified by column chromatography. Yield was 0.6 g of the title compound as a solid (Compound 27).

EXAMPLE 3

PYRAZOLO [3,4-c]PYRIDINES

Many pyrazolo [3,4-c]pyridines can be prepared from the appropriate pyridines as described in Example 1. In this example Aryl is an optionally substituted phenyl or pyridyl as heretofore described.

Preparation of various 1-Aryl-pyrazolo [3,4-c]pyridines:

A. Preparation of 1-aryl-5-bromopyrazolo [3,4-c]pyridine

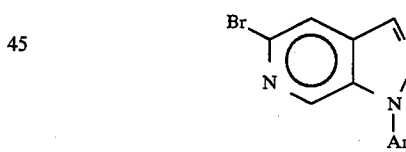

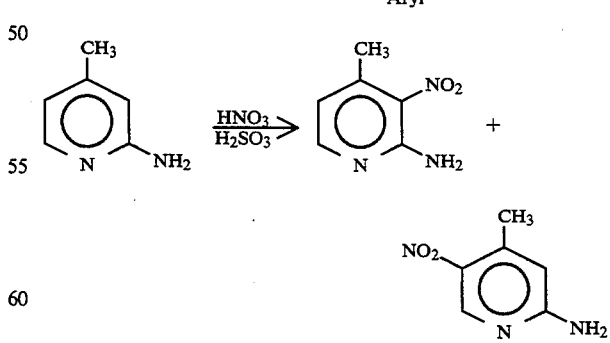

3-(and 5)-nitro-2-amino-4-methylpyridine

The nitration of 2-amino-4-methylpyridine was carried out as described by B. A. Fox, T. C. Threhall, Org. Syn Coll Vol. 5, p 346. This yielded a mixture of isomers in 75% yield.

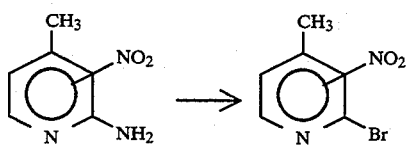

3-(and 5)-nitro-2-bromo-4-methylpyridine

The bromide exchange of the above nitro-amino-pyridine was carried out as described by C. F. H. Allen, John R. Thirtle, Org. Syn. Coll. Vol. 3, p 136, 1955. This gave a mixture of isomers in 40% yield. The 3 and 5-nitro isomers were separated by column chromatography to a corresponding yield ratio of 1:3.

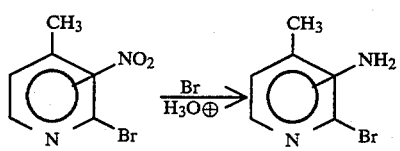

(both 3 & 5 NH₂ isomers)

3- (or 5)-amino-2-bromo-4-methlylpyridines

The corresponding nitropyridines were reduced as previously described using aqueous ethanol, iron powder and hydrochloric acid to give the amino pyridines in 80% yield.

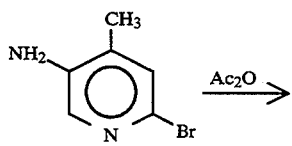

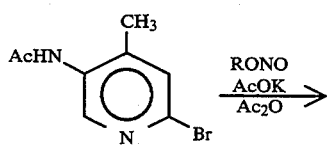

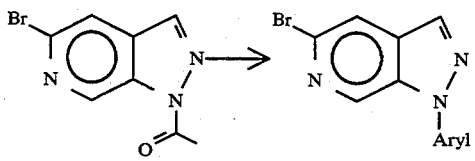

5-bromo pyrazolo [3,4-c]-pyridines 5-amino-2-bromo-4-methylpyridine was acylated and reacted as in Example 1. Similarly described is the synthesis of the 1-aryl-5-bromopyrazolo [3,4-c]pyridines (Compound No. 24).

B. Preparation of 5-ethanethio (or sulfonyl) - pyrazolo [3,4-c]pyridine

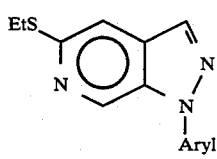

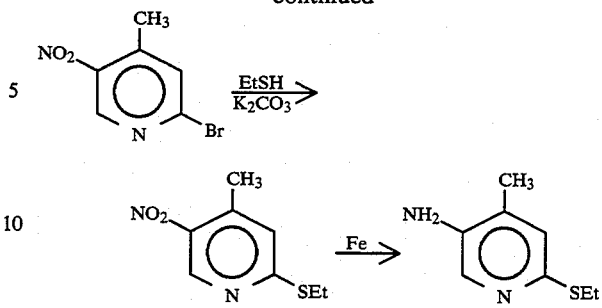

5-amino-2-ethanethio-4-methylpyridine

A solution of 8 g 2-bromo-4-methyl-5-nitropyridine 6.7 g potassium carbonate and 3.4 g ethanethiol in dimethyl formamide was heated to 70° C. for 6 hours. The solution was washed, dried and reduced under vacuum. Yield, 8 g of ethane-thiopyridine as an oil. This was reduced under standard conditions using iron powder, aqueous ethanol and hydrochloric acid to yield 7.0 g 5-amino-2-ethanethio-4-methylpyridine.

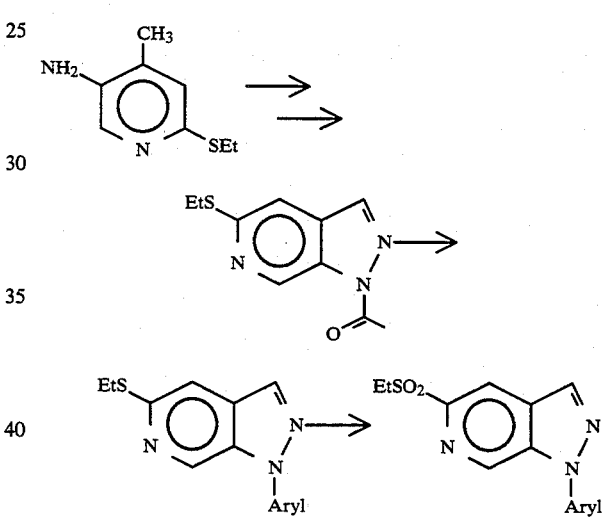

5-ethanethio (or sulfonyl-pyrazolo [3,4-c]pyridine

The above 5-amino pyridine was reacted as in Example 1 to give the pyrazolo [3,4-c]pyridine, then the 1-N-aryl-pyrazolo [3,4-c]pyridine (Compound No. 25). The 1-aryl-5-ethanethiopyrazolo [3,4-c]pyridine can be oxidized in cold (0° C.) methylene chloride with 2.1 g meta-chloroperoxy-benzoic acid, as previously described. This yielded the 5-ethanesulfonyl product (Compound No. 26).

C. Preparation of 1-aryl-pyrazolo [3,4-c]pyridine

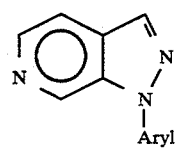

3-amino-4-methylpyridine

A solution of 2-bromo-3-nitro-4-methylpyridine in ethanol was reduced under 60 psi hydrogen using a 5% Pd. on carbon catalyst. This yields the 3-amino-4-methylpyridine quantitatively.

Pyrazolo [3,4-c]pyridine

Using the procedures described in Example 2, the corresponding amino-pyridine was reacted to form the pyrazolo [3,4-c]pyridine and the 1-aryl-pyrazolo [3,4-c]pyridine (Compound No. 23).

EXAMPLE 4

Preparation of pyrazolo [4,3-c]pyridazine

The preparation of the intermediate 3,6-dimethyl, 4-nitro-1-oxo pyridazine can be found in the following two references. Takanobu et al., Chem. Pharm. Bull. 9, 194 (1961) and Overberger et al., J. Am. Chem. Soc. 78, 1961 (1956);

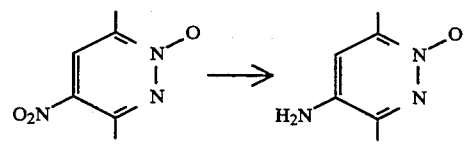

4-amino-3,6-dimethylpyridazine-N-oxide 3,6-dimethyl-4-nitropyridazine-N-oxide (1.0 g), 0.5 mL water, 5 mL ethanol, 0.025 mL conc HCl and 1.0 g Fe powder were stirred together and heated under reflux. After 30 minutes an additional 1.0 g of Fe and 2 drops conc HCl was added to the mixture. After 2 hours an additional 1 g Fe and 2 drops of conc HCl were added and heating continued for another 5 hours, whereupon 5 mL EtOH, 1 g Fe and 2 drops conc HCl were added. Reflux was continued for 20 hours. The reaction was cooled filtered through celite, the celite washed with $CH_3OH$ and the filtrate was evaporated to give an orange oil which crystallized on standing (0.88 g yield). Used without further purification.

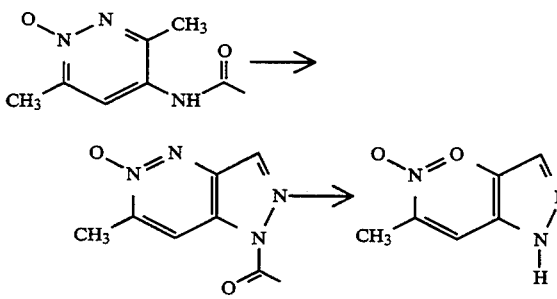

1-acetyl-6-methyl-5-oxapyrazolo-(4,3-c)pyridazine 4-amino-3,6-dimethylpyridazine-N-oxide (3 g, 16.5 mmol) and 3.5 mL acetic anhydride were dissolved in 35 mL benzene and heated to reflux. t-Butylnitrite (1.6 g, 16.5 mmol) was dissolved in 10 mL benzene and added over about 1 hour. Heating was continued for 3 hours. The solution was cooled and poured into water. Ethyl acetate was added and the organic extract was dried with $MgSO_4$ and evaporated to give a brown oil (one spot by TLC silica 5% $CH_3OH/CH_2Cl_2$) which solidified upon addition of ether. The solid was collected via vacuum filtration and used without further purification. (2.0 g)

1-H-6 methyl-5-oxapyrazolo (4,3-c)pyridazine 1.1 g of 1-acetyl-6-methyl-5-oxapyrazolo (4,3-c)-pyridazine was heated in 10 mL 10% HCl for 30 minutes. The resulting dark red solution was neutralized by addition of $NaHCO_3$. The resulting solid was extracted with ethyl acetate, dried with $MgSO_4$ and evaporated to give 1.1 g of a brown solid which was used without further purification.

1-[2,6 dichloro-4 trifluoromethylphenyl)-6-methyl-5-oxopyrazolo [4,3-c]pyridazine

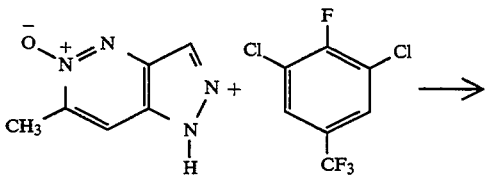

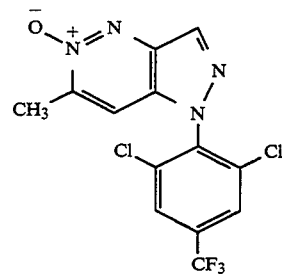

1 H-6-methyl-5-oxopyrazolo (4,5-c)pyridazine (1.0 g, 6.6 mmol), 3,5-dichloro-4-fluorobenzotrifluoride (1.46 g, 6.6 mmol) and freshly ground potassium carbonate (1.0 g, 7.2 mmol) were added to 18 g DMF and the resulting suspension stirred. A catalytic amount (about 0.05 g) of 18-crown-6 was added and the mixture heated to 60° C. for 30 minutes. The reaction mixture was cooled, poured into 2x volume of water and extracted with 50 mL ethyl acetate and then 50 mL $CH_2Cl_2$. The combined organic extracts were dried with $MgSO_4$ and evaporated to dryness. Ether (5 mL) was added to the resulting orange oil which then crystallized on standing. The solution was filtered to obtain 540 mg (24%) of an orange brown solid. (MP 201°–204°) (Compound No. 28)

EXAMPLE 5

PYRAZOLO [3,4-d]PYRIDAZINE

1-[2,4,6-trichlorophenyl]-4-hydroxypyrazolo [3,4-pyridazine

In general, the intermediate ethyl 4,4 diethoxy-2-ethoxymethylene-3-oxobutanoate can be prepared by known methods described in Bisagni et al., Tetrahedron, 29, 429 (1973) and the target pyridazines can be made by a method similar to that described in J. P. Marquet et al., Tetrahedron, 29, 435 (1973) with slight modifications within the preview of one skilled in the art.

Ethyl 4,4 diethoxy-2-ethoxymethylene-3-oxobutanoate (14.4 g, 0.052 mole) was added to a slight excess of 2,4,6-tri-chlorophenyl hydrazine (11.85 g, 0.056 mole) in 240 mL of dioxane and refluxed for 6 hours with removal of dioxane. The solution was cooled to 20° C. HCl was added and stirred for 16 hours. The organic phase was separated, dried and purified by chromatography. The resulting acetal was eluted with methylene chloride/ether.

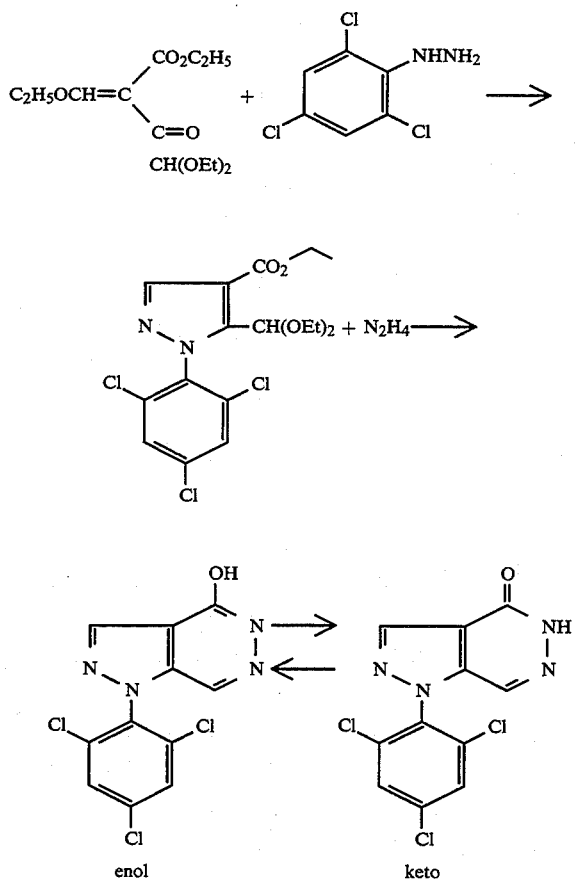

The acetal (11.8 g) was dissolved in acetic acid (220 mL) and refluxed. A solution of 4.8 g of hydrazine hydrate, in 30 mL of glacial acetic, was added and refluxing was continued. After 6 hours, no starting material was detected by gas chromatography. The cooled mixture was poured into 600 mL of ice-water. The solid formed was filtered off and recrystallized from dichloroethane to give 0.912 g pure product which can exist in either the keto form or enol form. (Compound 29)

When produced, the compounds of this invention are of a basic nature. The compounds can be reacted with strong acids to produce agriculturally acceptable salts. Therefore, any reference to the compound in the specification and claims is intended to encompass the agriculturally acceptable salts thereof within its purview.

These and other compounds made by the foregoing processes are set forth in Tables I, II and III which follows werein the various substitutent groups are indicated.

TABLE I

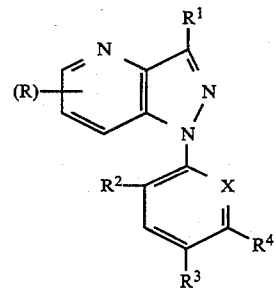

| Compound No. | R | $R^1$ | $R^2$ | $R^3$ | $R^4$ | X | $R^5$ | Physical Constant M.P. °C. or $n_D^{3°}$ |
|---|---|---|---|---|---|---|---|---|
| 1 | 5,6-dimethyl | H | Cl | $CF_3$ | H | $C-R^5$ | Cl | 135.0–136.0 |
| 2 | 5,6-dimethyl | H | Cl | $CF_3$ | H | N | | 114.0–115.0 |
| 3 | 5-$CH_3$ | H | Cl | $CF_3$ | H | $C-R^5$ | Cl | 94.0–98.0 |
| 4 | 7-$CH_3$ | H | Cl | $CF_3$ | H | N | | Oil |
| 5 | 5,7-dimethyl | H | Cl | $CF_3$ | H | N | | Oil |

TABLE II

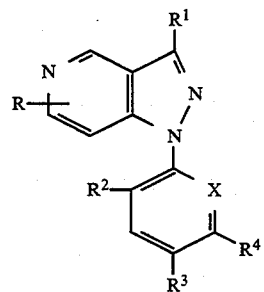

| Compound No. | R | $R^1$ | $R^2$ | $R^3$ | $R^4$ | X | $R^5$ |
|---|---|---|---|---|---|---|---|
| 6 | 4,6-$CF_3$ | H | Cl | $CF_3$ | H | N | |
| 7 | 4,6-$CH_3$ | H | Cl | $CF_3$ | H | N | |
| 8 | 4-$SC_2H_5$ | H | Cl | $CF_3$ | H | N | |
| 9 | 4-$SO_2C_2H_5$ | H | Cl | $CF_3$ | H | N | |
| 10 | 6-$SC_2H_5$ | H | Cl | $CF_3$ | H | N | |
| 11 | 4-CN | H | Cl | $CF_3$ | H | N | |
| 12 | H | H | Cl | $CF_3$ | H | N | |
| 13 | 4-$CH_3$ | H | Cl | $CF_3$ | H | N | |
| 14 | 4-$CH_3$, 6-CN | H | Cl | $CF_3$ | H | N | |
| 15 | 4-$CH_3$ | H | Cl | $CF_3$ | H | $C-R^5$ | Cl |
| 16 | 4-$CH_3$, 5-O | H | Cl | $CF_3$ | H | $C-R^5$ | Cl |
| 17 | 4-$CH_3$, 6-$SC_2H_5$ | H | Cl | $CF_3$ | H | N | |
| 18 | 4-$CH_3$, 5-O | H | Cl | $CF_3$ | H | N | |
| 19 | 4,6-$CF_3$ | H | Cl | $CF_3$ | H | $C-R^5$ | Cl |
| 27 | 4-$CH_2O$ | H | Cl | $CF_3$ | H | N | |

TABLE III

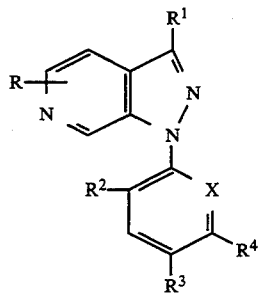

| Compound No. | R | R¹ | R² | R³ | R⁴ | X | R⁵ |
|---|---|---|---|---|---|---|---|
| 20 | 5-CH₃ | H | Cl | CF₃ | H | N | |
| 21 | 5-CH₃ | H | Cl | CF₃ | H | C—R⁵ | H |
| 22 | 7-Cl | H | Cl | CF₃ | H | N | |
| 23 | H | H | Cl | CF₃ | H | N | |
| 24 | 5-Br | H | Cl | CF₃ | H | N | |
| 25 | 5-SC₂H₅ | H | Cl | CF₃ | H | N | |
| 26 | 5-SO₂C₂H₅ | H | Cl | CF₃ | H | N | |

TABLE IV

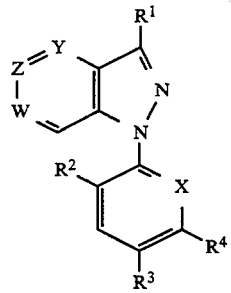

| Compound No. | Y | W | Z | R¹ | R² | R³ | R⁴ | X | R⁵ | Physical Constant M.P. °C. or n_D³ |
|---|---|---|---|---|---|---|---|---|---|---|
| 28 | N | CCH₃ | N—O | H | Cl | CF₃ | H | C—R⁵ | Cl | 201–204° |
| 29 | COH | N | N | H | Cl | Cl | H | C—R⁵ | Cl | — |

Other compounds included in the inventions are: 4-hydroxyl-1-[2,4,6-trichlorophenyl]pyrazolo [3,4-d]pyridazine, 1-(2,6-dichloro-4-trifluoromethylphenyl)-5-oxopyrazolo [4,3-c]pyridazine, and 4-hydroxy-1-[2,6-dichloro-4-trifluoromethyphenyl]pyrazolo [3,4-d]pyridazine.

This list of compounds is in no way intended to limit the invention.

HERBICIDAL SCREENING TESTS

The compounds listed in the foregoing tables were tested for herbicidal activity by various methods and at various rates of application. The results of some of these tests are given below. As one skilled in the art is aware, the results obtained in herbicidal screening tests are affected by a number of factors that are not readily controllable. Environmental conditions, such as amount of sunlight and water, soil type, soil pH, temperature and humidity, are examples of such factors. Other factors which can affect test results are the depth of planting and the application rate of the herbicide, as well as the nature of the crops being tested. Results will also vary from crop to crop and within the crop varieties.

PRE-EMERGENCE HERBICIDAL SCREENING TEST

On the day preceding treatment, seeds of several different weed species were planted in sandy loam soil in individual rows using one species per row across the width of a flat. The grassy weeds planted were green foxtail [SETVI] (Setaria viridis), wild oat [AVEFA] (Avena fatua), and water-grass [ECHCG] (Echinochloa crusgalli). Broadleaf weeds utilized were wild mustard [SINAi] (Brassica kaber), velvet-leaf [ABUTH] (Abutilon theophrasti), and annual morningglory (PHBPU) (Ipomoea purpurea). Ample seeds were planted to give about 20 to 40 seedlings per row, after emergence, depending upon the size of the plants.

Solutions of the test compounds were made by weighing out 400 (mg) of the test compound into a 60 mL wide-mouth bottle, then dissolving the compound in 25 mL acetone containing 1% Tween 20 (polyoxyethylene sorbitan monolaurate emulsifier). Additional solvents, not exceeding 5 mL, were used if needed to dissolve the compound. A 20.5 mL aliquot was then taken from the solution and diluted with 25 mL of an acetone:water mixture (19:1) containing 1% Tween 20 to form a sprayable solution.

The flats were placed in a greenhouse at 21°–29.5° C., and watered by sprinkling. One day after planting, the flats were sprayed with the spray solution calibrated to deliver 400L/ha. The application rate was 4.0 kg/ha.

The flats were then returned to the greenhouse and water daily by sprinkling. The degree of weed control was estimated and recorded 3 weeks after treatment, as percentage control compared to the growth of the same species in an untreated check flat of the same age.

The percent control is the total injury to the plants due to all factors, including inhibited germination, killing of the plant tissue after emergence, stunting, malformation, chlorosis and other types of injury. The control ratings vary from 0 to 100 percent, where 0 represents no effect with growth equal to the untreated control, and 100 represents complete kill; a dash indicates that no test was performed at that level of application.

POST-EMERGENCE HERBICIDAL EVALUATION

The soil was prepared and seeded with the same varieties as described for the pre-emergence test. The flats were placed in the greenhouse at 21°–29° C. and watered by sprinkling. The seeds of the weed species were planted 10–12 days before treatment. The flats were sprayed with solution at a rate of 4 kg/ha, using a spray solution as prepared in the pre-emergence test.

The flats were returned to the greenhouse after spraying and watered daily without wetting the foliage. Three weeks after treatment the degree of weed control was estimated and recorded as percentage control compared to the growth of the same species in an untreated check flat of the same age. The percent control ratings were assigned on the basis as for the pre-emergence evaluation.

The results are listed in Table V below.

-continued

| Common Name | Scientific Name | ABR |
|---|---|---|
| Hemp sesbania | *Sebania exaltata* | MATCH SEBEX STEME |

TABLE V
GREENHOUSE HERBICIDAL TEST RESULTS

| | APPLICATION | | WEED SPECIES PERCENT INJURY | | | | | |
|---|---|---|---|---|---|---|---|---|
| Compound No. | Rate kg/ha | Method | AVEFA | ECHCG | SETVI | ABUTH | PHBPU | SINAR |
| 1 | 4.0 | PES | 90 | 100 | 100 | 100 | 100 | 100 |
| | 4.0 | POS | 95 | 100 | 100 | 100 | 100 | 100 |
| 2 | 4.0 | PES | 90 | 100 | 100 | 100 | 100 | 100 |
| | 4.0 | POS | 95 | 100 | 100 | 100 | 100 | 100 |
| 3 | 4.0 | PES | 70 | 100 | 100 | 100 | 90 | 100 |
| | 4.0 | POS | 20 | 100 | 95 | 100 | 100 | 100 |
| 4 | 4.0 | PES | 0 | 0 | 0 | 0 | 0 | 0 |
| | 4.0 | POS | 20 | 50 | 90 | 100 | 100 | 15 |
| 5 | 4.0 | PES | 0 | 0 | 0 | 0 | 0 | 0 |
| | 4.0 | POS | 0 | 5 | 5 | 60 | 60 | 30 |
| 8 | 4.0 | PES | 15 | 95 | 100 | 100 | 98 | 98 |
| | 4.0 | POS | 5 | 100 | 100 | 100 | 100 | 100 |
| 9 | 4.0 | PES | 10 | 70 | 90 | 70 | 10 | 15 |
| | 4.0 | POS | 5 | 40 | 70 | 100 | 100 | 20 |
| 10 | 4.0 | PES | 90 | 100 | 100 | 100 | 100 | 100 |
| | 4.0 | POS | 100 | 100 | 100 | 100 | 100 | 100 |
| 11 | 4.0 | PES | 95 | 100 | 100 | 100 | 100 | 100 |
| | 4.0 | POS | 100 | 100 | 100 | 100 | 100 | 100 |
| 12 | 4.0 | PES | 10 | 15 | 100 | 100 | 30 | 0 |
| | 4.0 | POS | 30 | 30 | 100 | 100 | 100 | 50 |
| 13 | 4.0 | PES | 25 | 98 | 100 | 100 | 100 | 100 |
| | 4.0 | POS | 50 | 85 | 100 | 100 | 100 | 100 |
| 14 | 4.0 | PES | 0 | 0 | 100 | 100 | 80 | 100 |
| | 4.0 | POS | 5 | 15 | 40 | 100 | 100 | 100 |
| 20 | 4.0 | PES | 20 | 100 | 100 | 70 | 10 | 60 |
| | 4.0 | POS | 80 | 100 | 100 | 100 | 100 | 100 |
| 21 | 4.0 | PES | 30 | 80 | 100 | 100 | 0 | 100 |
| | 4.0 | POS | 40 | 95 | 100 | 100 | 100 | 95 |
| 22 | 4.0 | PES | 0 | 5 | 75 | 90 | 0 | 0 |
| | 4.0 | POS | 0 | 0 | 15 | 100 | 90 | 15 |
| 28 | 4.0 | PES | 100 | 100 | 100 | 100 | 100 | 100 |
| | 4.0 | POS | 100 | 100 | 100 | 100 | 100 | 100 |
| 29 | 4.0 | PES | 85 | 100 | 100 | 100 | 95 | 100 |
| | 4.0 | POS | 10 | 100 | 70 | 100 | 100 | 85 |

Another series of tests was undertaken in accordance with the procedure described above, except that differing quantities of herbicide were used. Those quantities were achieved by dilution of the original spray solution.

The weed species were as follows:

| Common Name | Scientific Name | ABR |
|---|---|---|
| Wild oat | *Avena fatua* | ALOMY AVEFA |
| Broadleaf signalgrass | *Brachiaria platyphylla* | BRAPP |
| Watergrass | *Echinochloa crusgalli* | ECHCG |
| Green foxtail | *Setaria viridis* | SETFA |
| Velvetleaf | *Abutilon theophrasti* | ABUTH |
| Pigweed | | AMARE CASOB |
| Morningglory | *Ipomoea* | IPOSS |

In addition to the foregoing weed species, the herbicides were also tested against various crop species. The crop species were as follows:

| | | WI |
|---|---|---|
| Soybean | *Glycine max* | SOY |
| Cotton | *Gossypium hirsutum* | COT |
| Sugarbeet | *Beta vulgaris* | SB |
| Wheat | *Triticum aestivum* | WH |
| Rice | *Oryzae Sativa* | RC |
| Milo | *Sorghum bicolor* | ML |
| Corn | *Zea mays* | CN |

The results of these tests are set forth in Table VI and Table VII below.

TABLE VI

| APPLICATION | | | WEED SPECIES PERCENT INJURY | | | | | | | |
|---|---|---|---|---|---|---|---|---|---|---|
| Cmpd. No. | Rate kg/ha | Method | ALOMY | AVEFA | BRAPP | ECHCG | SETVI | ABUTH | AMARE | CASOB |
| 1 | 2.00 | PES | 90 | 5 | 90 | 100 | 100 | 100 | 100 | 35 |
| | | POS | 15 | 40 | 0 | 85 | 25 | 100 | 100 | 10 |
| | 1.00 | PES | 20 | 0 | 85 | 100 | 100 | 100 | 100 | 15 |
| | | POS | 20 | 45 | 0 | 65 | 0 | 100 | 100 | 0 |
| | 0.50 | PES | 10 | 0 | 75 | 80 | 100 | 100 | 100 | 0 |
| | | POS | 30 | 20 | 0 | 15 | 0 | 100 | 100 | 0 |
| | 0.25 | PES | — | — | — | — | — | — | — | — |
| | | POS | — | — | — | — | — | — | — | — |
| 2 | 2.00 | PES | 85 | 65 | 100 | 95 | 100 | 50 | 100 | 0 |
| | | POS | 55 | 75 | 50 | 80 | 90 | 60 | 60 | 15 |
| | 1.00 | PES | 50 | 15 | 60 | 90 | 100 | 50 | 100 | 0 |

TABLE VI-continued

| | | | | | | | | | | |
|---|---|---|---|---|---|---|---|---|---|---|
| | | POS | 40 | 35 | 20 | 55 | 15 | 20 | 20 | 0 |
| | 0.50 | PES | 5 | 5 | 10 | 0 | 100 | 0 | 75 | 0 |
| | | POS | 25 | 20 | 0 | 30 | 5 | 0 | 0 | 0 |
| | 0.25 | PES | — | — | — | — | — | — | — | — |
| | | POS | — | — | — | — | — | — | — | — |
| 3 | 2.00 | PES | 10 | 0 | 50 | 10 | 85 | 45 | 75 | 80 |
| | | POS | — | — | — | — | — | — | — | — |
| | 1.00 | PES | 0 | 0 | 0 | 0 | 50 | 15 | 40 | 0 |
| | | POS | — | — | — | — | — | — | — | — |
| | 0.50 | PES | 0 | 0 | 0 | 0 | 0 | 0 | 0 | 0 |
| | | POS | — | — | — | — | — | — | — | — |
| | 0.25 | PES | 0 | 0 | 20 | 20 | 100 | 30 | 10 | 0 |
| | | POS | 0 | 0 | 5 | 45 | 20 | 60 | 100 | 30 |
| 6 | 2.00 | PES | — | — | — | — | — | — | — | — |
| | | POS | — | — | — | — | — | — | — | — |
| | 1.00 | PES | 0 | 0 | 0 | 0 | 40 | — | 100 | — |
| | | POS | 5 | 0 | — | 25 | 30 | 100 | 95 | 100 |
| | 0.50 | PES | 0 | 0 | — | — | 30 | 0 | | |
| | | POS | 5 | 0 | — | 20 | 20 | 100 | 100 | 100 |
| | 0.25 | PES | 0 | 0 | — | 0 | 0 | 0 | — | — |
| | | POS | 0 | 0 | 10 | — | 20 | 100 | 95 | 75 |
| 7 | 2.00 | PES | — | — | — | — | — | — | — | — |
| | | POS | — | — | — | — | — | — | — | — |
| | 1.00 | PES | — | — | — | — | — | — | — | — |
| | | POS | 10 | 50 | 10 | 10 | 55 | 100 | 100 | 50 |
| | 0.50 | PES | — | — | — | — | — | — | — | — |
| | | POS | — | — | — | — | — | — | — | — |
| | 0.25 | PES | — | — | — | — | — | — | — | — |
| | | POS | 10 | 40 | 0 | 0 | 5 | 30 | 100 | 15 |
| 8 | 2.00 | PES | — | — | — | — | — | — | — | — |
| | | POS | — | — | — | — | — | — | — | — |
| | 1.00 | PES | 10 | 40 | 65 | 95 | too | 100 | 100 | 40 |
| | | POS | 10 | 20 | 10 | 30 | 45 | 85 | 100 | 30 |
| | 0.50 | PES | — | — | — | — | — | — | — | — |
| | | POS | — | — | — | — | — | — | — | — |
| | 0.25 | PES | 0 | 10 | 30 | 20 | 65 | 20 | 98 | 0 |
| | | POS | 10 | 20 | 10 | 20 | 30 | 80 | 90 | 30 |
| 9 | 2.00 | PES | 10 | 0 | 45 | 15 | 35 | 50 | 100 | 20 |
| | | POS | 10 | 15 | 5 | 5 | 25 | 30 | 98 | 30 |
| | 1.00 | PES | 0 | 0 | 0 | 0 | 0 | 35 | 100 | 40 |
| | | POS | 0 | 0 | 5 | 10 | 15 | 25 | 95 | 30 |
| | 0.50 | PES | — | — | — | — | — | — | — | — |
| | | POS | — | — | — | — | — | — | — | — |
| | 0.25 | PES | — | — | — | — | — | — | — | — |
| | | POS | — | — | — | — | — | — | — | — |
| 10 | 2.00 | PES | — | — | — | — | — | — | — | — |
| | | POS | — | — | — | — | — | — | — | — |
| | 1.00 | PES | — | — | — | — | — | — | — | — |
| | | POS | — | — | — | — | — | — | — | — |
| | 0.50 | PES | — | — | — | — | — | — | — | — |
| | | POS | — | — | — | — | — | — | — | — |
| | 0.25 | PES | 0 | 30 | 0 | 5 | 65 | 0 | 70 | 0 |
| | | POS | 20 | 30 | 15 | 15 | 30 | 99 | 100 | 5 |
| 11 | 2.00 | PES | — | — | — | — | — | — | — | — |
| | | POS | — | — | — | — | — | — | — | — |
| | 1.00 | PES | 80 | 55 | 100 | 100 | 100 | 100 | 100 | 60 |
| | | POS | 98 | 100 | 98 | 98 | 100 | 100 | 100 | 100 |
| | 0.50 | PES | — | — | — | — | — | — | — | — |
| | | POS | — | — | — | — | — | — | — | — |
| | 0.25 | PES | 30 | 20 | 35 | 60 | 100 | 100 | 100 | 20 |
| | | POS | 65 | 65 | 15 | 50 | 75 | 100 | 100 | 65 |
| 12 | 2.00 | PES | — | — | — | — | — | — | — | — |
| | | POS | — | — | — | — | — | — | — | — |
| | 1.00 | PES | 0 | 0 | 45 | 0 | 30 | 40 | 65 | 10 |
| | | POS | 15 | 20 | 5 | 10 | 25 | 98 | 100 | 25 |
| | 0.50 | PES | — | — | — | — | — | — | — | — |
| | | POS | — | — | — | — | — | — | — | — |
| | 0.25 | PES | 0 | 0 | 0 | 0 | 0 | 0 | 15 | 0 |
| | | POS | 5 | 10 | 0 | 0 | 5 | 98 | 70 | 10 |
| 19 | 2.00 | PES | — | — | — | — | — | — | — | — |
| | | POS | — | — | — | — | — | — | — | — |
| | 1.00 | PES | 70 | 10 | 95 | 95 | 100 | 100 | 100 | 100 |
| | | POS | 0 | 5 | 0 | 5 | 55 | 100 | 100 | 95 |
| | 0.50 | PES | 30 | 10 | 95 | 98 | 100 | 100 | 100 | 100 |
| | | POS | 0 | 5 | 5 | 5 | 35 | 100 | 95 | 100 |
| | 0.25 | PES | 0 | 0 | 95 | 30 | 95 | 100 | 100 | 100 |
| | | POS | 0 | 5 | 5 | 5 | 20 | 100 | 100 | 40 |
| 20 | 2.00 | PES | — | — | — | — | — | — | — | — |
| | | POS | — | — | — | — | — | — | — | — |
| | 1.00 | PES | 0 | 20 | 0 | 0 | 0 | 10 | 0 | 10 |
| | | POS | 5 | 5 | 15 | 20 | 55 | 100 | 100 | 100 |
| | 0.50 | PES | 0 | 0 | 0 | 0 | 0 | 0 | 0 | 0 |

TABLE VI-continued

| | | | | | | | | | | |
|---|---|---|---|---|---|---|---|---|---|---|
| | | POS | 5 | 5 | 0 | 10 | 50 | 100 | 100 | 30 |
| | 0.25 | PES | 0 | 0 | 0 | 0 | 0 | 0 | 0 | 0 |
| | | POS | 5 | 10 | 0 | 10 | 35 | 100 | 35 | 10 |
| 21 | 2.00 | PES | — | — | — | — | — | — | — | — |
| | | POS | — | — | — | — | — | — | — | — |
| | 1.00 | PES | 20 | 25 | 10 | 10 | 98 | 100 | 100 | 0 |
| | | POS | 0 | 20 | 0 | 0 | 70 | 100 | 100 | 15 |
| | 0.50 | PES | 0 | 10 | 0 | 10 | 30 | 15 | 0 | 0 |
| | | POS | 0 | 10 | 0 | 0 | 55 | 100 | 100 | 0 |
| | 0.25 | PES | 0 | 0 | 0 | 0 | 0 | 10 | 0 | 0 |
| | | POS | 0 | 0 | 0 | 0 | 30 | 100 | 70 | 0 |
| 28 | 0.5 | PES | 65 | 75 | 98 | 100 | 100 | 100 | 100 | — |
| | | POS | — | — | — | — | — | — | — | — |
| | 0.25 | PES | 20 | 60 | 75 | 100 | 100 | 98 | 100 | — |
| | | POS | 30 | 45 | 35 | 90 | 55 | 100 | 100 | — |

| | APPLICATION | | WEED SPECIES PERCENT INJURY | | | | |
|---|---|---|---|---|---|---|---|
| Cmpd. No. | Rate kg/ha | Method | IPOSS | MATCH | SEBEX | STEME | XANPE |
| 1 | 2.00 | PES | 95 | 100 | 100 | 100 | 0 |
| | | POS | 100 | 40 | 100 | 100 | 0 |
| | 1.00 | PES | 100 | 100 | 100 | 50 | 0 |
| | | POS | 100 | 0 | 100 | 100 | 0 |
| | 0.50 | PES | 80 | 50 | 95 | 50 | 0 |
| | | POS | 90 | 10 | 95 | 20 | 0 |
| | 0.25 | PES | — | — | — | — | — |
| | | POS | — | — | — | — | — |
| 2 | 2.00 | PES | 75 | 100 | 100 | 0 | 0 |
| | | POS | 100 | 0 | 95 | 0 | 0 |
| | 1.00 | PES | 70 | 70 | 95 | 0 | 0 |
| | | POS | 75 | 0 | 80 | 0 | 0 |
| | 0.50 | PES | 20 | 0 | 0 | 0 | 0 |
| | | POS | 75 | 0 | 60 | 0 | 0 |
| | 0.25 | PES | — | — | — | — | — |
| | | POS | — | — | — | — | — |
| 3 | 2.00 | PES | 5 | 90 | 100 | 90 | 5 |
| | | POS | — | — | — | — | — |
| | 1.00 | PES | 0 | 50 | 25 | 50 | 0 |
| | | POS | — | — | — | — | — |
| | 0.50 | PES | 0 | 0 | 10 | — | 0 |
| | | POS | — | — | — | — | — |
| | 0.25 | PES | 100 | 0 | 15 | — | 20 |
| | | POS | 100 | 0 | 100 | 0 | 15 |
| 6 | 2.00 | PES | — | — | — | — | — |
| | | POS | — | — | — | — | — |
| | 1.00 | PES | 10 | 100 | — | 45 | — |
| | | POS | 88 | 100 | — | 100 | — |
| | 0.50 | PES | — | 100 | — | 20 | — |
| | | POS | 90 | 90 | — | 85 | — |
| | 0.25 | PES | 0 | 0 | — | 5 | — |
| | | POS | 100 | 60 | — | 50 | — |
| 7 | 2.00 | PES | — | — | — | — | — |
| | | POS | — | — | — | — | — |
| | 1.00 | PES | — | — | — | — | — |
| | | POS | 100 | 90 | — | 70 | — |
| | 0.50 | PES | — | — | — | — | — |
| | | POS | — | — | — | — | — |
| | 0.25 | PES | — | — | — | — | — |
| | | POS | 100 | 60 | — | 45 | — |
| 8 | 2.00 | PES | — | — | — | — | — |
| | | POS | — | — | — | — | — |
| | 1.00 | PES | 45 | 100 | — | 98 | — |
| | | POS | 100 | 100 | — | 20 | — |
| | 0.50 | PES | — | — | — | — | — |
| | | POS | — | — | — | — | — |
| | 0.25 | PES | 0 | 100 | — | 0 | — |
| | | POS | 90 | 100 | — | 20 | — |
| 9 | 2.00 | PES | 0 | 100 | — | 0 | — |
| | | POS | 65 | 20 | — | 10 | — |
| | 1.00 | PES | 0 | 95 | — | 0 | — |
| | | POS | 65 | 0 | — | 0 | — |
| | 0.50 | PES | — | — | — | — | — |
| | | POS | — | — | — | — | — |
| | 0.25 | PES | — | — | — | — | — |
| | | POS | — | — | — | — | — |
| 10 | 2.00 | PES | — | — | — | — | — |
| | | POS | — | — | — | — | — |
| | 1.00 | PES | — | — | — | — | — |
| | | POS | — | — | — | — | — |
| | 0.50 | PES | — | — | — | — | — |
| | | POS | — | — | — | — | — |
| | 0.25 | PES | 0 | 50 | — | 0 | — |
| | | POS | 100 | 50 | — | 50 | — |

TABLE VI-continued

| | | | | | | | | |
|---|---|---|---|---|---|---|---|---|
| 11 | 2.00 | PES | — | — | — | — | — | |
| | | POS | — | — | — | — | — | |
| | 1.00 | PES | 98 | 100 | — | 100 | — | |
| | | POS | 100 | 100 | — | 100 | — | |
| | 0.50 | PES | — | — | — | — | — | |
| | | POS | — | — | — | — | — | |
| | 0.25 | PES | 70 | 100 | — | 100 | — | |
| | | POS | 100 | 100 | — | 20 | — | |
| 12 | 2.00 | PES | — | — | — | — | — | |
| | | POS | — | — | — | — | — | |
| | 1.00 | PES | 15 | 95 | — | 0 | — | |
| | | POS | 100 | — | — | 0 | — | |
| | 0.50 | PES | — | — | — | — | — | |
| | | POS | — | — | — | — | — | |
| | 0.25 | PES | 10 | 0 | — | 0 | — | |
| | | POS | 95 | — | — | 0 | — | |
| 19 | 2.00 | PES | — | — | — | — | — | |
| | | POS | — | — | — | — | — | |
| | 1.00 | PES | 100 | 100 | — | 65 | — | |
| | | POS | 100 | 100 | — | 0 | — | |
| | 0.50 | PES | 50 | 100 | — | 60 | — | |
| | | POS | 100 | 100 | — | 0 | — | |
| | 0.25 | PES | 0 | 100 | — | 20 | — | |
| | | POS | 95 | 100 | — | 0 | — | |
| 20 | 2.00 | PES | — | — | — | — | — | |
| | | POS | — | — | — | — | — | |
| | 1.00 | PES | 50 | 100 | — | 0 | — | |
| | | POS | 100 | 80 | — | 0 | — | |
| | 0.50 | PES | 20 | 0 | — | 0 | — | |
| | | POS | 95 | 65 | — | 0 | — | |
| | 0.25 | PES | 0 | 0 | — | 0 | — | |
| | | POS | 100 | 10 | — | 0 | — | |
| 21 | 2.00 | PES | — | — | — | — | — | |
| | | POS | — | — | — | — | — | |
| | 1.00 | PES | 0 | 0 | — | 0 | — | |
| | | POS | 95 | 0 | — | 0 | — | |
| | 0.50 | PES | 0 | 0 | — | 0 | — | |
| | | POS | 85 | 0 | — | 0 | — | |
| | 0.25 | PES | 0 | 0 | — | 0 | — | |
| | | POS | 70 | 0 | — | 0 | — | |
| 28 | 0.5 | PES | 60 | 100 | — | — | 70 | |
| | | | — | — | — | — | — | |
| | 0.25 | PES | 45 | 100 | — | — | 45 | |
| | | POS | 100 | 55 | — | — | — | |

TABLE VII

| APPLICATION | | | CROP SPECIES PERCENT INJURY | | | | | | |
|---|---|---|---|---|---|---|---|---|---|
| Cmpd. No. | Rate kg/ha | Method | CN | ML | RC | WH | COT | SB | SOY |
| 1 | 2.00 | PES | 50 | 95 | 20 | 30 | 25 | 100 | 20 |
| | | POS | 30 | 20 | 10 | 90 | 70 | 85 | 45 |
| | 1.00 | PES | 15 | 55 | 20 | 20 | 0 | 100 | 15 |
| | | POS | 20 | 15 | 10 | 80 | 70 | 75 | 20 |
| | 0.50 | PES | 0 | 5 | 0 | 5 | 0 | 95 | 0 |
| | | POS | 30 | 5 | 0 | 45 | 85 | 45 | 10 |
| | 0.25 | PES | — | — | — | — | — | — | — |
| | | POS | — | — | — | — | — | — | — |
| 2 | 2.00 | PES | 35 | 75 | 10 | 25 | 0 | 95 | 0 |
| | | POS | 60 | 15 | 20 | 70 | 40 | 40 | 25 |
| | 1.00 | PES | 0 | 0 | 0 | 10 | 0 | 90 | 0 |
| | | POS | 40 | 5 | 0 | 60 | 20 | 40 | 10 |
| | 0.50 | PES | 0 | 0 | 0 | 0 | 0 | 50 | 0 |
| | | POS | 20 | 0 | 0 | 40 | 10 | 15 | 10 |
| | 0.25 | PES | — | — | — | — | — | — | — |
| | | POS | — | — | — | — | — | — | — |
| 3 | 2.00 | PES | 10 | 10 | 75 | 0 | 5 | 10 | 20 |
| | | POS | — | — | — | — | — | — | — |
| | 1.00 | PES | 0 | 0 | 15 | 0 | 5 | 0 | 0 |
| | | POS | 5 | 80 | 10 | 20 | — | 100 | 85 |
| | 0.50 | PES | 0 | 0 | 0 | 0 | 0 | 0 | 0 |
| | | POS | 5 | 40 | 10 | 10 | — | 100 | 40 |
| | 0.25 | PES | — | — | — | — | — | — | — |
| | | POS | 0 | 10 | 5 | 5 | — | 100 | 15 |
| 6 | 2.00 | PES | — | — | — | — | — | — | — |
| | | POS | — | — | — | — | — | — | — |
| | 1.00 | PES | 0 | — | 0 | 0 | — | 0 | — |
| | | POS | 0 | — | 10 | 10 | — | 100 | 70 |
| | 0.50 | PES | — | — | 0 | 0 | — | 0 | 0 |
| | | POS | 0 | — | 10 | 5 | — | 100 | 70 |
| | 0.25 | PES | 0 | — | 0 | 0 | — | 0 | 0 |
| | | POS | 0 | — | 10 | 5 | — | 100 | 40 |

TABLE VII-continued

| APPLICATION | | | CROP SPECIES PERCENT INJURY | | | | | | |
|---|---|---|---|---|---|---|---|---|---|
| Cmpd. No. | Rate kg/ha | Method | CN | ML | RC | WH | COT | SB | SOY |
| 7 | 2.00 | PES | — | — | — | — | — | — | — |
| | | POS | — | — | — | — | — | — | — |
| | 1.00 | PES | — | — | — | — | — | — | — |
| | | POS | 20 | — | 10 | 5 | — | 100 | 60 |
| | 0.50 | PES | — | — | — | — | — | — | — |
| | | POS | — | — | — | — | — | — | — |
| | 0.25 | PES | — | — | — | — | — | — | — |
| | | POS | 15 | — | 10 | 5 | — | 60 | 45 |
| 8 | 2.00 | PES | — | — | — | — | — | — | — |
| | | POS | — | — | — | — | — | — | — |
| | 1.00 | PES | 15 | — | 0 | 25 | — | 65 | 0 |
| | | POS | 15 | — | 20 | 15 | — | 100 | 40 |
| | 0.50 | PES | — | — | — | — | — | — | — |
| | | POS | — | — | — | — | — | — | — |
| | 0.25 | PES | 0 | — | 0 | 0 | — | 10 | 0 |
| | | POS | 15 | — | 10 | 10 | — | 100 | 30 |
| 9 | 2.00 | PES | 15 | — | 25 | 0 | — | 10 | 30 |
| | | POS | 10 | — | 5 | 10 | — | 50 | 50 |
| | 1.00 | PES | 10 | — | 15 | 0 | — | 10 | 0 |
| | | POS | 5 | — | 5 | 0 | — | 30 | 55 |
| | 0.50 | PES | — | — | — | — | — | — | — |
| | | POS | — | — | — | — | — | — | — |
| | 0.25 | PES | — | — | — | — | — | — | — |
| | | POS | — | — | — | — | — | — | — |
| 10 | 2.00 | PES | — | — | — | — | — | — | — |
| | | POS | — | — | — | — | — | — | — |
| | 1.00 | PES | — | — | — | — | — | — | — |
| | | POS | — | — | — | — | — | — | — |
| | 0.50 | PES | — | — | — | — | — | — | — |
| | | POS | — | — | — | — | — | — | — |
| | 0.25 | PES | 5 | — | 0 | 0 | — | 100 | 0 |
| | | POS | 20 | — | 10 | 10 | — | 40 | 30 |
| 11 | 2.00 | PES | — | — | — | — | — | — | — |
| | | POS | — | — | — | — | — | — | — |
| | 1.00 | PES | 35 | — | 25 | 45 | — | 100 | 35 |
| | | POS | 50 | — | 70 | 98 | — | 100 | 100 |
| | 0.50 | PES | — | — | — | — | — | — | — |
| | | POS | — | — | — | — | — | — | — |
| | 0.25 | PES | 10 | — | 10 | 10 | — | 100 | 10 |
| | | POS | 30 | — | 30 | 35 | — | 100 | 90 |
| 12 | 2.00 | PES | — | — | — | — | — | — | — |
| | | POS | — | — | — | — | — | — | — |
| | 1.00 | PES | 10 | — | 20 | 0 | — | 10 | 0 |
| | | POS | 25 | — | 5 | 25 | — | 60 | 60 |
| | 0.50 | PES | — | — | — | — | — | — | — |
| | | POS | — | — | — | — | — | — | — |
| | 0.25 | PES | 0 | — | 0 | 0 | — | 0 | 0 |
| | | POS | 15 | — | 5 | 15 | — | 45 | 20 |
| 13 | 2.00 | PES | — | — | — | — | — | — | — |
| | | POS | — | — | — | — | — | — | — |
| | 1.00 | PES | 0 | — | 10 | 0 | — | 0 | 12 |
| | | POS | 12 | — | 20 | 10 | — | 58 | 35 |
| | 0.50 | PES | — | — | — | — | — | — | — |
| | | POS | — | — | — | — | — | — | — |
| | 0.25 | PES | 0 | — | 0 | 0 | — | 0 | 0 |
| | | POS | 15 | — | 12 | 10 | — | 15 | 20 |
| 20 | 2.00 | PES | — | — | — | — | — | — | — |
| | | POS | — | — | — | — | — | — | — |
| | 1.00 | PES | 0 | — | 0 | 10 | — | 0 | 30 |
| | | POS | 10 | — | 10 | 10 | — | 100 | 35 |
| | 0.50 | PES | 0 | — | 0 | 0 | — | 0 | 10 |
| | | POS | 0 | — | 10 | 10 | — | 95 | 40 |
| | 0.25 | PES | 0 | — | 0 | 0 | — | 0 | 0 |
| | | POS | 0 | — | 10 | 10 | — | 80 | 15 |
| 21 | 2.00 | PES | — | — | — | — | — | — | — |
| | | POS | — | — | — | — | — | — | — |
| | 1.00 | PES | 10 | — | 0 | 10 | — | 40 | 0 |
| | | POS | 5 | — | 0 | 0 | — | 100 | 40 |
| | 0.50 | PES | 0 | — | 0 | 0 | — | 0 | 0 |
| | | POS | 5 | — | 0 | 0 | — | 40 | 15 |
| | 0.25 | PES | 0 | — | 0 | 0 | — | 0 | 0 |
| | | POS | 0 | — | 0 | 0 | — | 10 | 35 |

METHOD OF APPLICATION

The compounds of the present invention are useful as herbicides and can be applied in a variety of ways known to those skilled in the art, at various concentrations. The compounds are useful in controlling the growth of undesirable vegetation by pre-emergence or post-emergence application to the locus where control is desired. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as granules, as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of the seeds or plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are free-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplet are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, such as the Freons, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as a package containing the herbicide together with other ingredients of the formulation (diluents, emulsifiers, surfactants etc.). The formulations can also be prepared by a tank mix method, in which the ingredients are obtained separately and combined at the grower site.

The compounds of the present invention are also useful when combined with other herbicides and/or defoliants, dessicants, growth inhibitors, and the like. These other materials can comprise from about 5% to about 95% of the active ingredients in the formulations. These combinations frequently provided a higher level of effectiveness in controlling weeds and often provide results unattainable with separate formulations of the individual herbicides.

Examples of other herbicides, defoliants, dessicants and plant growth inhibitors with which the compounds of this invention can be combined are:

acetanilide herbicides such as alachlor, 2-chloro-2',6'-diethyl-N-(methoxymethyl) acetanilide; acetochlor, 2-chloro-2'-methyl-6'ethyl-N-ethoxymethyl acetanilide; metolachlor, 2-chloro-2'-methyl-6'ethyl-N-methoxy-isopropyl-2-acetanilide;

chlorophenoxy herbicides such as 2,4-D, 2,4,5-T, MCPA, MCPB, 2,4-DB, 2,4-DEB, 4-CPA, 2,4,5-TB, and silvex;

carbamate herbicides such as propham, chlorpropham, swep, and barban;

thiocarbamate and dithiocarbamate herbicides such as CDEC, metham-sodium, EPTC, diallate, PEBC, and vernolate;

substituted urea herbicides such as norea, dichloral, urea, chloroxuron, cycluron, fenuron, monuron, monuron TCA, diuron, linuron, monolinuron neburon, buturon and trimeturon;

substituted triazine herbicides such as simazine, chlorazine, desmetryne, norazine, ipazine, prometryn, atrazine, trietazine, simetone, prometone, propazine and ametryne;

chlorinated aliphatic acid herbicides such as TCA and dalapon;

chlorinated benzoic acid and phenylacetic acid herbicides such as 2,3,6-TBA, dicamba, tricamba, chloramben, fenac, PBA, 2-methoxy-3,6-dichlorophenYl acetic acid, 3-meth-oxy-2,6-dichlorophenyl acetic acid, 2-methoxy-3,5,6-trichloro-phenyl acetic acid, and 2,4-dichloro-3-nitro benzoic acid;

sulfonylurea herbicides such as chlorosulfuron, chlorimuron, chlorimuron ethyl and bensulfuron ethyl;

imidazoline herbicides such as imazapyr, imazaquin, and imazethapyr;

aryloxyphenoxy herbicides such as fluazifop-p-butyl, fenoxaprop, and quizalofop-p;

diphenyl ether herbicides such as fomesafen, chlomethyoxyfen and bifenox;

oxime herbicides such as sethoxydim and clethodim;

pyrazole and pyridine derivatives; substituted 1,3-cyclohexanedione compounds, including 2-(2-substituted benzoyl)-1,3-cyclohexanediones;

and such compounds as aminotriazole, maleic hydrazide, phenylmercury acetate, endothal, technical chlordane, CDCPA, diquat, erbon, DNC, DNBP, dichlobenil, DPA, diphenamide, dipropalin, trifluralin, solan, dicryl, merphos, DMPA, DSMA, MSMA, potassium azide, acrolein, benefin, bensulide, AMS, bromacil, 2-(3,4-dichlorophenyl)-4-methyl-1,2,4-oxazoli-dine-3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, sesone, terbacil, terbutol, TCBA, nitralin, sodium tetraborate, calcium cyanamide, S,S,S-tributylphosphorotrithioate and propanil, isopropyl amine salt of N-phosphonomethyl glycine, trimethylsulfonium salts of N-phosphonomethyl glycine.

GENERAL

These formulations can be applied to the areas where control is desired by conventional methods. Dust and liquid compositions, for example, can be applied by the use of power-dusters, boom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

The following are examples of typical formulations.

| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

| 5% granules: | 5 parts active compound |
| | 0.25 part epichlorohydrin |
| | 0.25 part cetyl polyglycol ether |
| | 3.5 parts polyethylene glycol |
| | 91 part kaolin (particle size 0.3–0.8 mm) |

Granules are formed by mixing the active compound with epichlorohydrin and dissolving the mixture in 6 parts of acetone. The polyethylene glycol and cetyl polyglycol ether are then added. The resultant solution is sprayed on the kaolin and the acetone evaporated in vacuo.

| Wettable powders: | |
|---|---|
| 70% | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40% | 40 parts active compound |
| | 5 parts sodium lignin sulfonate |
| | 1 part sodium dibutylnaphthalene sulfonic acid |
| | 54 parts silicic acid |
| 25% | 25 parts active compound |
| | 4.5 parts calcium lignin sulfate |
| | 1.9 parts Champagne chalk/hydroxyethyl cellulose (1:1) |
| | 1.5 parts sodium dibutylnaphthalene sulfonate |
| | 19.5 silicic acid |
| | 19.5 parts Champagne chalk |
| | 28.1 parts kaolin |
| 25%: | 25 parts active compound |
| | 2.5 parts isooctylphenoxy-polyethylene-ethanol |
| | 1.7 parts Champagne chalk/hydroxyethyl cellulose (1:1) |
| | 8.3 parts sodium aluminum silicate |
| | 16.5 parts kieselguhr |
| | 46 parts kaolin |
| 10%: | 10 parts active compound |
| | 3 parts of a mixture of sodium salts of saturated fatty alcohol sulfates |
| | 5 parts naphthalenesulfonic acid/formaldehyde condensate |
| | 82 parts kaolin |

These wettable powders are prepared by intimately mixing the active compounds with the additives in suitable mixers, and grinding the resulting mixture in mills or rollers.

| Emulsifiable concentrate: | |
|---|---|
| 25%: | 25 parts active substance |
| | 2.5 parts epoxidized vegetable oil |
| | 10 parts of an alkylarylsulfonate/fatty alcohol polyglycol ether mixture |
| | 5 parts dimethylformamide |
| | 57.5 parts xylene |

The amount of the present compositions which constitute a herbicidally effective amount depends upon the nature of the seeds or plants to be controlled. The rate of application of active ingredients varies from about 0.01 to about pounds per acre, preferably about 0.10 to about 10 pounds per acre with the actual amount depending on the overall costs and the desired results. It will be readily apparent to one skilled in the art that compositions exhibiting lower herbicidal activity will require a higher dosage than more active compounds for the same degree of control.

What is claimed is:

1. A substituted fused pyrazolo compound having the formula

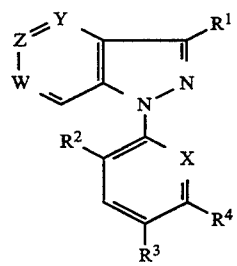

in which Z and one of Y and W are N or N-O and the other of Y and W is C-R wherein R is hydrogen; halogen; nitro; cyano; alkyl; alkoxyalkyl; acetoxymethyl; hydroxymethyl; haloalkyl; formyl; alkylcarbonyl; carboxy or a salt thereof; COO alkyl; azido ($N_3$); amino; substituted amino wherein the substituents are alkyl, alkoxy, hydroxy, formyl, alkylcarbonyl, alkoxycarbonylalkyloxy, alkoxycarbonylalkylthio, alkoxycarbonylalkylidenecarbonyl, hydroxycarbonylalkoxy, hydroxycarbonylthio, cyanoalkoxy, hydroxycarbonyl-alkylidenecarbonyl, alkylsulfonyl, haloalkylsulfonyl, aminocarbonyl, (di)alkylaminocarbonyl, alkoxycarbonyl, alkoxyalkyl, hydroxycarbonylalkyl, alkoxycarbonylalkyk, and amino; carboxyamido; substituted carboxyamido wherein said substituents can be selected from alkyl, alkylsulfonyl, and haloalkylsulfonyl; sulfonamido wherein the N is substituted with hydrogen and/or alkyl; $VR^6$ wherein V is O or $S(O)_m$ and $R^6$ is selected from the group hydrogen, alkyl, haloalkyl, cyanoalkyl, alkoxycarbonylalkyl, hydroxycarbonylalkyl and aminocarbonylalkyl wherein the N is optionally substituted with alkyl;

m is 0 to 2;

$R^1$ is hydrogen or halogen;

$R^2$ is hydrogen, nitro, halogen, cyano, alkylthio, alkylsulfinyl, alkylsulfonyl, or alkoxy;

$R^3$ is halogen, haloalkyl, cyano, alkylthio, alkylsulfinyl, or alkylsulfonyl;

$R^4$ is hydrogen or halogen;

X is N or C-$R^5$;

wherein $R^5$ is hydrogen, haloalkyl, halogen, cyano, nitro, alkylthio, alkylsulfinyl, alkylsulfonyl, or alkoxy; or an agriculturally acceptable salt thereof.

2. A compound according to claim 1 wherein R is hydrogen, halogen, lower alkyl, lower alkoxy, cyano, nitro, alkoxyalkyl, haloalkyl, alkylthio, alkylsulfonyl or akoxycarbonylalkylthio, $R^1$ is hydrogen, $R^2$ is hydrogen or halogen, $R^3$ is halogen or haloalkyl and $R^4$ is hydrogen.

3. A compound according to claim 2 wherein X is N.

4. A compound according to claim 2 wherein X is C-$R^5$.

5. A compound according to claim 3 wherein $R^3$ is chloro or trifluoromethyl.

6. A compound according to claim 4 wherein $R^5$ is hydrogen or halogen and $R^3$ is chloro or trifluoromethyl.

7. An herbicidal composition which comprises an herbicidally effective amount of a substituted pyrazolopyridazine as claimed in claim 1, with an inert carrier or diluent suitable for use with herbicides.

8. A method for controlling undesirable weed pests which comprises applying to the locus where control is desired an herbicidally effective amount of a novel substituted pyrazolo as claimed in claim 1.

9. A method according to claim 8 wherein undesirable weed pests are controlled in the presence of a crop.

10. A method according to claim 9 wherein the crop is corn.

11. A method according to claim 9 wherein the crop is rice.

* * * * *